(12) United States Patent
Ginesi et al.

(10) Patent No.: US 6,973,833 B2
(45) Date of Patent: Dec. 13, 2005

(54) WAFER AND METHOD

(75) Inventors: Donald Ginesi, Lakeland, FL (US); Donald R. Augenstein, Pittsburgh, PA (US); Keith Bergstrom, Herminie, PA (US); Calvin R. Hastings, Pittsburgh, PA (US); Christopher B. Laird, Pittsburgh, PA (US); Benjamin Lane, Phoenix, MD (US); Brian Lipford, Bel Air, MD (US)

(73) Assignee: Caldon, Inc., Pittsburgh, PA (US)

( * ) Notice: Subject to any disclaimer, the term of this patent is extended or adjusted under 35 U.S.C. 154(b) by 0 days.

(21) Appl. No.: 10/107,852

(22) Filed: Mar. 12, 2002

(65) Prior Publication Data

US 2003/0172737 A1 Sep. 18, 2003

(51) Int. Cl.$^7$ .......................... G01H 1/00; G01H 11/00; G01M 1/22; G01F 1/32; G01F 1/42

(52) U.S. Cl. ..................... 73/660; 73/861.61; 73/861.23

(58) Field of Search ............................ 73/866.5, 861.18, 73/861.23, 861.21, 861.25, 861.61, 628, 660

(56) References Cited

U.S. PATENT DOCUMENTS

| 4,141,246 A | * | 2/1979 | Randolph ................ 73/861.21 |
| 6,016,023 A | * | 1/2000 | Nilsson et al. ............. 310/341 |
| 6,101,885 A | * | 8/2000 | Touzin et al. ............ 73/861.22 |

* cited by examiner

Primary Examiner—Hezron Williams
Assistant Examiner—Tamiko Bellamy
(74) Attorney, Agent, or Firm—Ansel M. Schwartz

(57) ABSTRACT

A wafer for placement in a pipe. The wafer includes a housing having an outer surface and an orifice adapted to allow fluid flowing in the pipe to pass through the housing. The housing has at least a first port extending into the housing from the outer surface for holding a first acoustic transducer. The wafer includes means for attaching the housing to the pipe. A method for obtaining information about fluid in a pipe.

22 Claims, 7 Drawing Sheets

WAFER AND METHOD

FIELD OF THE INVENTION

The present invention is related to a wafer which connects to a pipe through which fluid in the pipe can flow and which has an acoustic transducer for introducing ultrasonic signals into the pipe. More specifically, the present invention is related to a wafer which connects to a pipe that maintains a constant force against the transducer to better couple the transducer to the wafer.

BACKGROUND OF THE INVENTION

Acoustic transducers are commonly used for various types of measurements of fluids and pipes. The acoustic transducers are mounted to the pipe either by being placed on the surface of the pipe, or in holes that are drilled into the pipe to better allow the transducer to directly couple with the interior of the pipe. Of utmost importance in the placement of the acoustic transducer on the pipe, be it on the surface or in a hole drilled in the pipe, is the alignment of the transducer. Whether the acoustic transducer utilizes a bounce path with respect to the signal it produces to receive the signal back and analyze data obtained with the signal, or where the acoustic transducer transmits and ultrasonic signal across the pipe to an opposing acoustic transducer which receives the signal, the alignment of the acoustic transducer or acoustic transducers is critical so the ultrasonic signals are properly received. Accordingly, the placement and alignment of the acoustic transducers can be a time consuming, tedious step that must be done carefully, and is susceptible to error. An example of a device having sensors that is available from Controlotron clamps onto the pipe.

The present invention provides for a relatively simple technique for introducing acoustic transducers, as well as other types of transducers, into a pipe, where the alignment and the placement has been preestablished and is accurate. The present invention further allows the straightforward removal or repair of the transducers.

SUMMARY OF THE INVENTION

The present invention pertains to a wafer for placement in a pipe. The wafer comprises a housing having an outer surface and an orifice adapted to allow fluid flowing in the pipe to pass through the housing. The housing has at least a first port extending into the housing from the outer surface for holding a first acoustic transducer. The wafer comprises means for attaching the housing to the pipe.

The present invention pertains to a method for obtaining information about fluid in a pipe. The method comprises the steps of placing a wafer with a flange of a pipe. There is the step of flowing fluid through an orifice of the wafer as the fluid flows through the pipe. There is the step of transmitting ultrasonic signals from the first acoustic transducer in a first port of the wafer into the fluid in the pipe.

BRIEF DESCRIPTION OF THE DRAWINGS

In the accompanying drawings, the preferred embodiment of the invention and preferred methods of practicing the invention are illustrated in which:

FIG. 3 is a detailed view of the bottom of the first port in contact with the orifice at which the window screws in.

DETAILED DESCRIPTION

Figure 1:
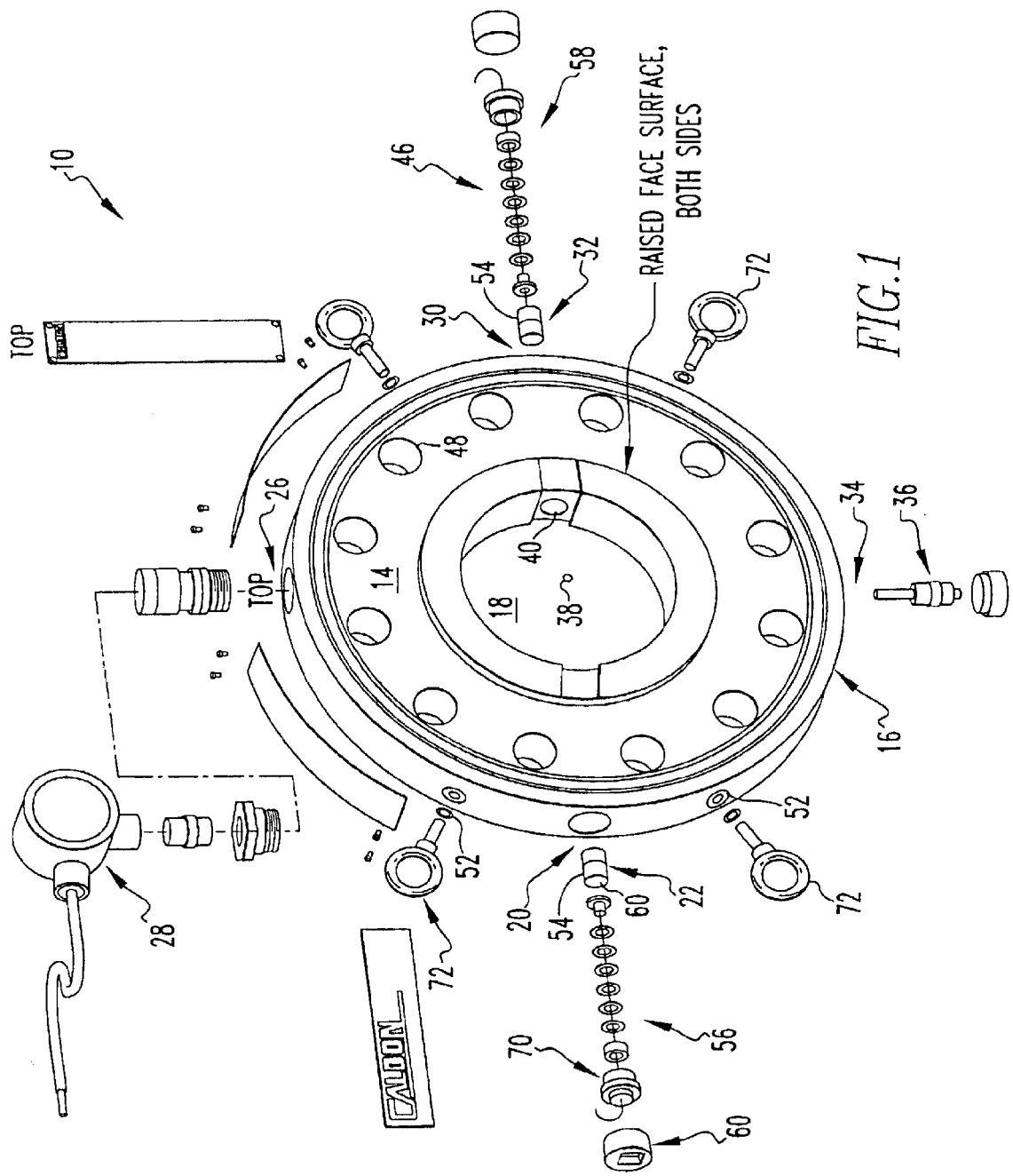
FIG. 1 is an assembly view of a wafer of the present invention.
Figure 14:
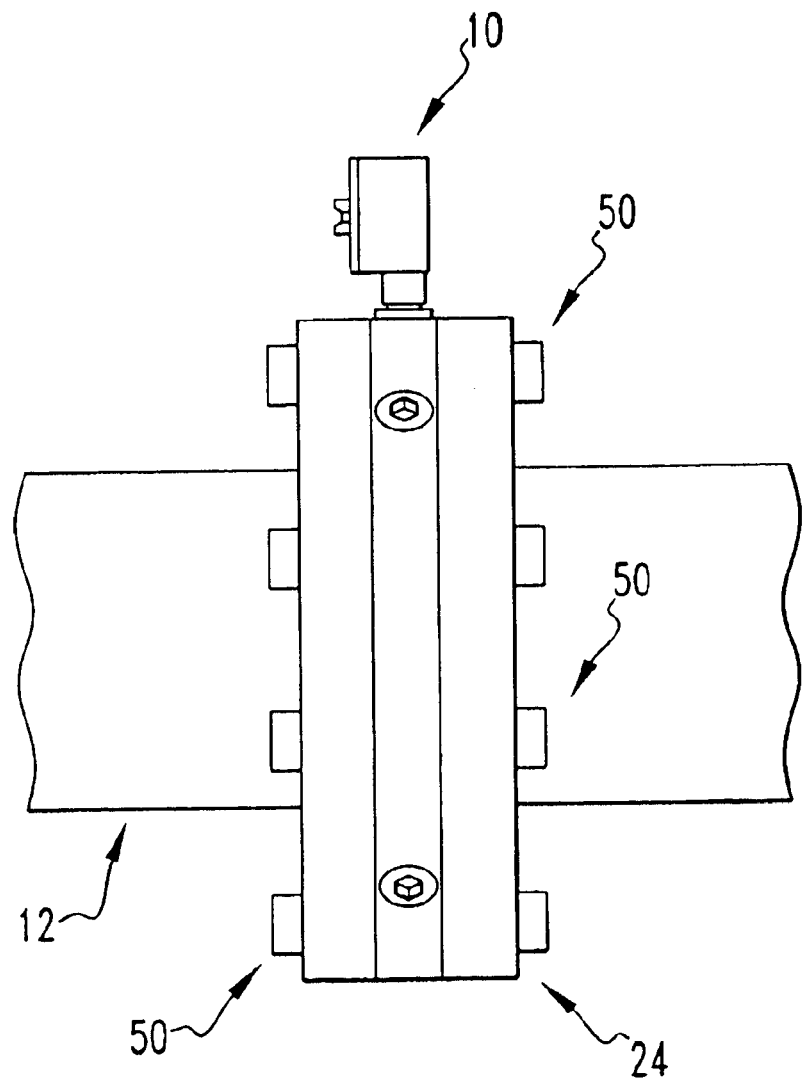
FIG. 14 is a side view of the wafer with flanges of a pipe.

Referring now to the drawings wherein like reference numerals refer to similar or identical parts throughout the several views, and more specifically to FIGS. 1 and 14 thereof, there is shown a wafer 10 for placement in a pipe 12. The wafer 10 comprises a housing 14 having an outer surface 16 and an orifice 18 adapted to allow fluid flowing in the pipe 12 to pass through the housing 14. The housing 14 has at least a first port 20 extending into the housing 14 from the outer surface 16 for holding a first acoustic transducer. The wafer 10 comprises means for attaching the housing 14 to the pipe 12.

Preferably, the housing 14 includes at least a second port 26 extending into the housing 14 from the outer surface 16 for holding a junction box 28 which is in electrical communication with the first transducer 22. The housing 14 preferably includes a third port 30 extending into the housing 14 from the outer surface 16 for holding a second acoustic transducer which is in electrical communication with the junction box 28. Preferably, the housing 14 includes a fourth port 34 extending into the housing 14 from the outer surface 16 for holding a temperature sensor 36 in electrical communication with the junction box 28. The first, second, third and fourth ports 20, 26, 30, 34 preferably extend radially inward towards the center 38 of the housing 14.

Figure 4:
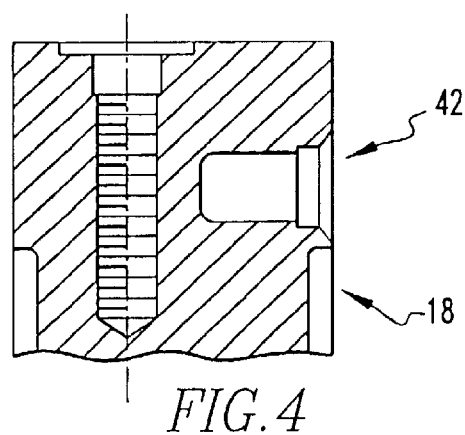
FIG. 4 is a detailed view of the channel relative to a screw to hold the first acoustic transducer to the wafer.
Figure 6:
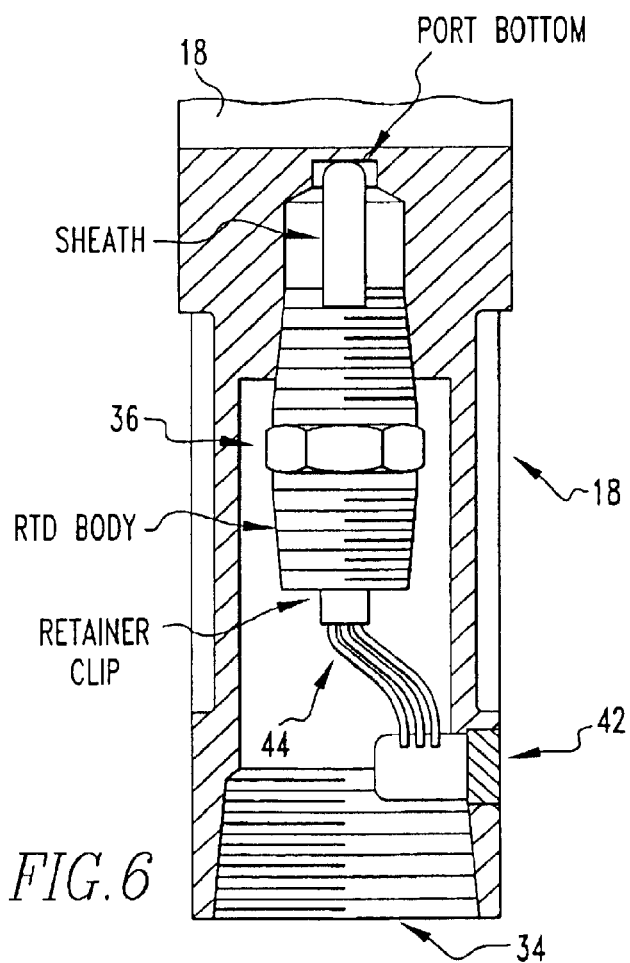
FIG. 6 is a detailed view of the fourth port with a temperature sensor.
Figure 10:
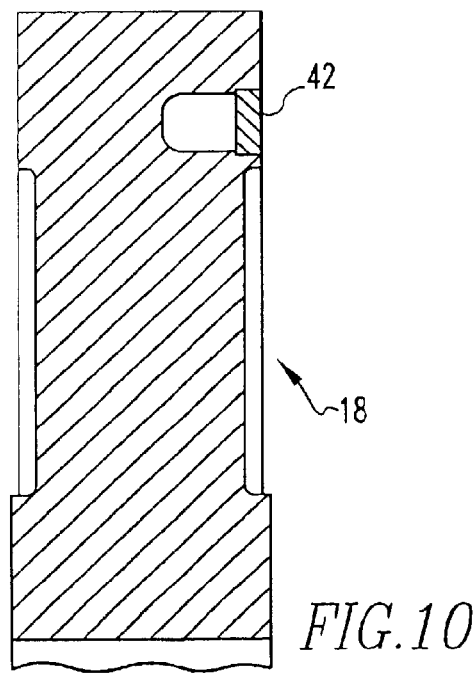
FIG. 10 is a sectional view of the channel in the housing.

Preferably, the housing 14 includes a window 40 disposed between each of the first and third ports 20, 30 and the orifice 18. The housing 14 preferably has a channel 42 adapted for wires 44 from the first transducer 22, second transducer 32 and temperature sensor 36 to extend to the junction box 28, as shown in FIGS. 4, 6 and 10. Preferably, the first port 20 and the third port 30 are in alignment for ultrasonic signals from the first transistor to communicate with the second transducer 32 after the ultrasonic signals pass through the orifice 18. The radius of the orifice 18 preferably is essentially equal to the inside radius of the pipe 12 so there is essentially no disruption of the fluid flowing through the pipe 12.

Preferably, the wafer 10 includes biasing means 46 for pressing against the first and second acoustic transducer to couple the first and second acoustic transducers to the respective window 40 when the first and second acoustic transducer are attached to the housing 14. The attaching means 24 preferably includes a series of holes 48 dispersed in the housing 14 and bolts 50 that fit through the holes 48 and are adapted to screw into holes 48 in a flange of the pipe 12. Preferably, the housing 14 has plugs 52 extending into the housing 14 positioned about the first and third ports 20, 30 to which are screwed into the housing 14 for lifting purposes.

Figure 2:
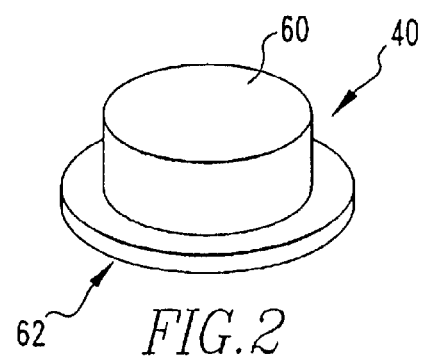
FIG. 2 is a perspective view of a window.
Figure 7:
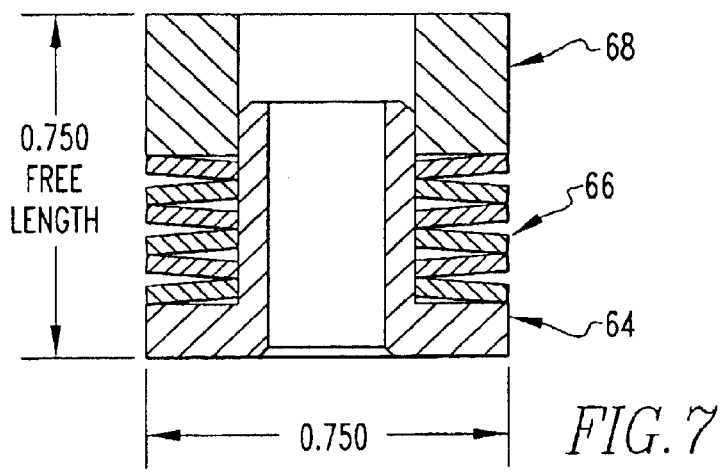
FIG. 7 is an assembled sectional view of the spring means.
Figure 8:
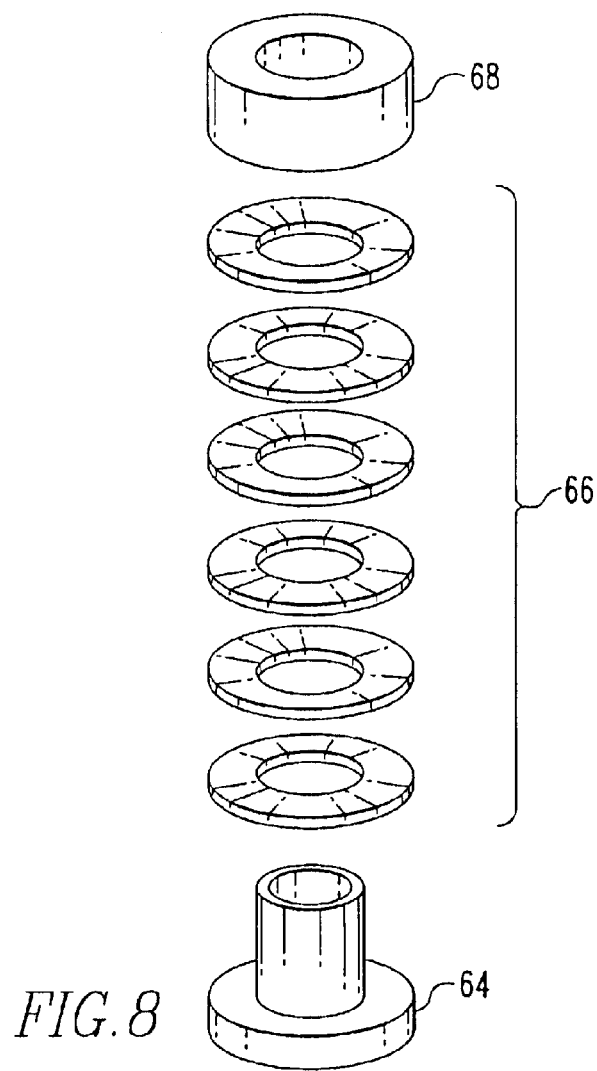
FIG. 8 is an exploded view of the spring means.

The first and second acoustic transducers preferably include a crystal 54 disposed in the first and third ports 20, 30, respectively, when the first and second acoustic transducers are attached to the housing 14, and wherein the biasing means 46 includes a first spring means 56 and a second spring means 58 disposed in the first port 20 and the third port 30, respectively, and adapted to press against the respective crystal 54 to couple the respective crystal 54 against the window 40 of the respective port, as shown in FIGS. 7 and 8. Preferably, the window 40 has a top 60 and a bottom 62 which are flat and are polished to at least 16 micro inch rms, as shown in FIG. 2. Each spring means preferably includes a guide 64 which contacts the respective crystal 54 top, a plurality of washers 66 disposed on the guide 64, a spacer 68 disposed on the washers 66 and a screw top 70 disposed on the spacer 68 and screws to the housing 14 and holds the respective spring means in its respective port.

The present invention pertains to a method for obtaining information about fluid in a pipe 12. The method comprises the steps of placing a wafer 10 with a flange of a pipe 12. There is the step of flowing fluid through an orifice 18 of the wafer 10 as the fluid flows through the pipe 12. There is the step of transmitting ultrasonic signals from the first acoustic transducer in a first port 20 of the wafer 10 into the fluid in the pipe 12.

Preferably, the transmitting step includes the step of transmitting the ultrasonic signals from the first transducer 22 through a window 40 into the fluid in the pipe 12 having a polished surface of at least 16 rms. The transmitting step preferably includes the step of maintaining continuously a force against a crystal 54 in the first port 20 of the first acoustic transducer to force the crystal 54 against the window 40 while the crystal 54 produces the ultrasonic signals.

Preferably, there is the step of sending electrical signals between the first transducer 22 and a junction box 28 disposed in a second port 26 of the wafer 10 through wires 44 that extend along a channel 42 in the wafer 10. The maintaining step preferably includes the step of screwing a screw top 70 to the first port 20 of the wafer 10 which compresses washers 66 in the first port 20 that in turn press against a guide 64 in the first port 20 that contacts the top of the crystal 54, with a wire of the crystal 54 extending through the guide 64, the washers 66, and the screw top 70. Preferably, there is the step of receiving the ultrasonic signals at a second transducer 32 disposed in a second port 26 of the wafer 10.

Figure 3:
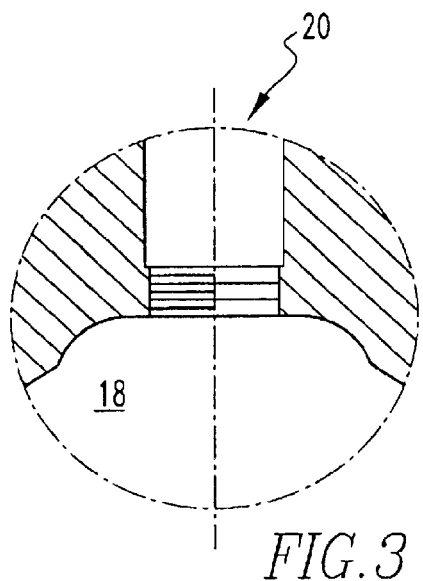
Figure 9:
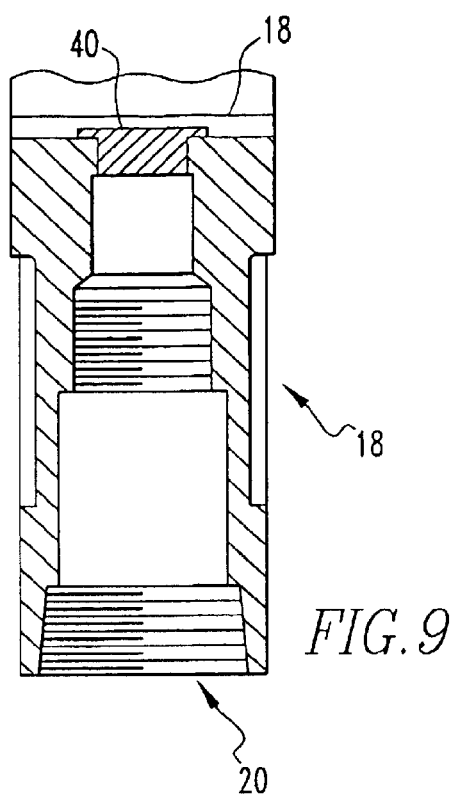
FIG. 9 is a sectional view of the first port with the window in position.
Figure 13:
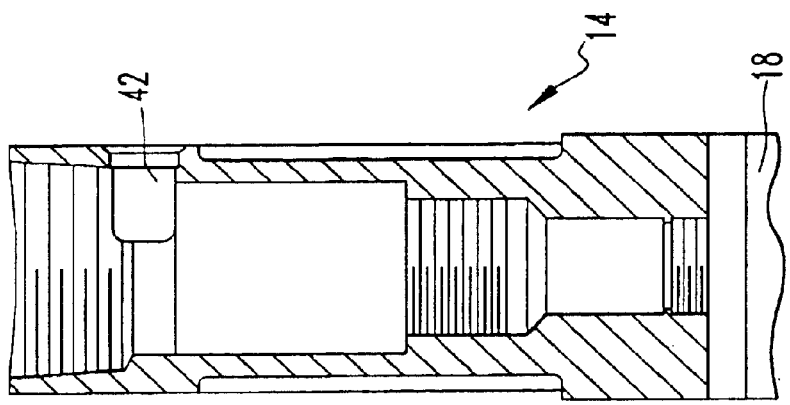
FIG. 13 is a sectional view of the first port.
Figure 12:
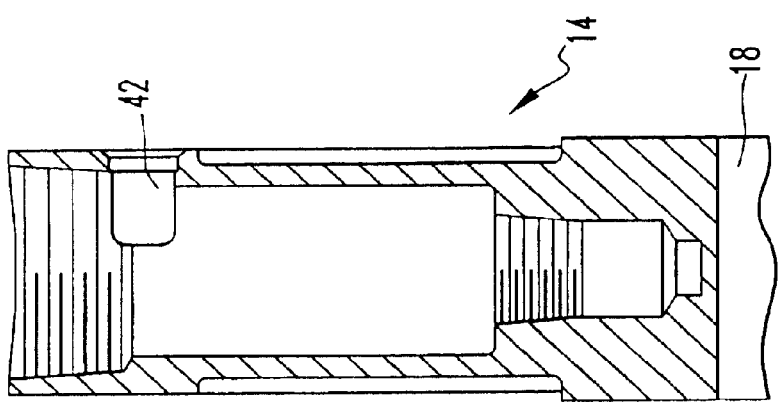
FIG. 12 is a sectional view of the fourth port.
Figure 11:
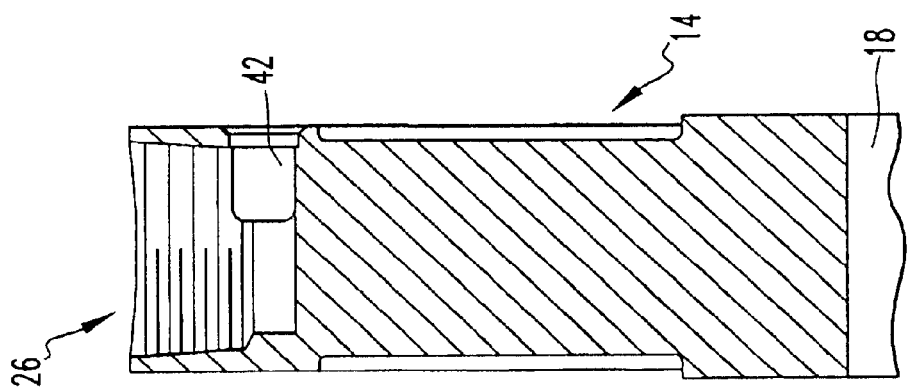
FIG. 11 is a sectional view of the second port.

In the operation of the preferred embodiment, a wafer 10 is formed by machining a housing 14 that conforms to the pipe 12 to which it is going to be fitted. This means that an orifice 18 having a radius that is essentially the same as the radius of the inner radius of the pipe 12 is formed in the housing 14, and a series of holes 48 are formed in the housing 14 about the orifice 18 that align with the holes 48 in the flanges of the pipe 12 to which the wafer 10 will attach. In addition, a first port 20, as shown in FIGS. 9 and 13, as shown in FIG. 11, second port 26, third port 30, as shown in FIGS. 9 and 13, and fourth port 34, as shown in FIGS. 6 and 12, are formed at the 3 o'clock position, at the top 60 or 12 o'clock position, at the bottom 62 or 6 o'clock position and the 9 o'clock position, respectively. The first port and the third port 30 are drilled from the outer surface 16 through to the orifice 18. The opening that is created into the orifice 18 from the first port 20 and the third port 30 is threaded at its end and a window 40 is screwed into the opening and then seal welded in place to close the opening to the orifice 18, as shown in FIGS. 2 and 3.

The reason that the first port 20 and the third port 30 are drilled through to the orifice 18 is because a polished surface of at least 16 micro inch rms is desired at the interface between the orifice 18 and the port to allow for a better coupling of the respective transducer that will fit into the respect port. This desired polished surface is more easily obtained by placing a window 40 that has its top 60 and bottom 62 flat and polished to at least 16 rms micro inch and then seal welded in place, rather than attempting to polish the material that would be left in place after the respective port is drilled for the respective transducer.

In addition, a channel 42 is formed in the outer surface 16 of the housing 14 that extends between all the ports so wiring from each of the ports can extend along the channel 42 to the second port 26 that holds a junction box 28, as shown in FIGS. 11–13. Moreover, a plug 52 is formed in the housing 14 at about the 2 o'clock and 4 o'clock, and 8 o'clock and 10 o'clock positions in which eyebolts 72 will be screwed into the wafer 10 to the housing 14 for lifting purposes, as shown in FIG. 4.

Figure 5:
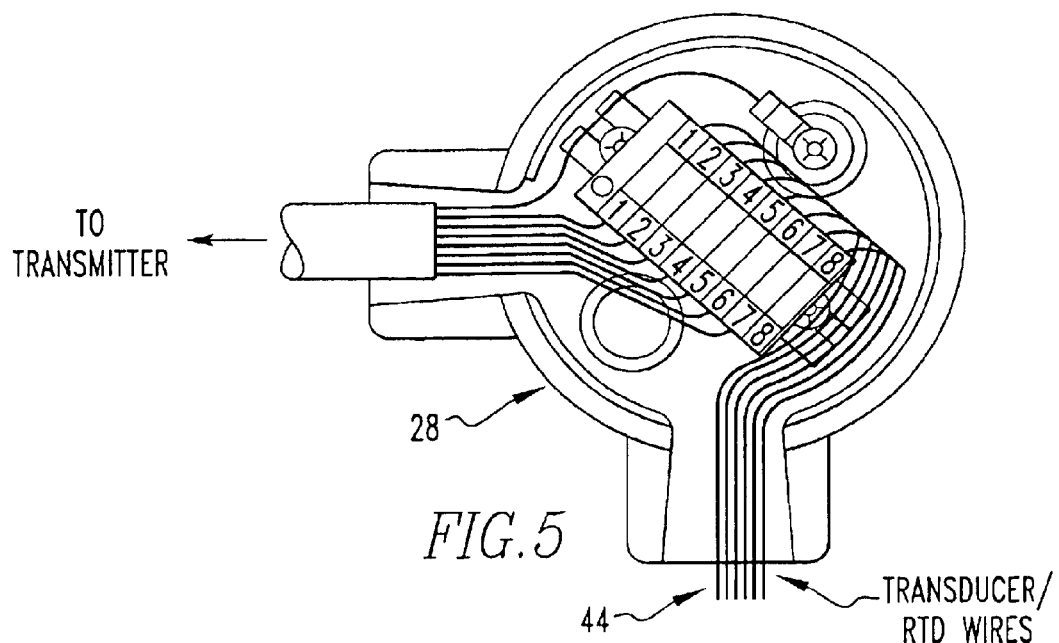
FIG. 5 is a detailed view of the junction box.

A junction box 28, as shown in FIG. 5, is threaded into the second port 26. The junction box 28 is connected to a transmitter. A temperature sensor 36 is mounted into the housing 14 by being threaded into the fourth port 34. A first acoustic transducer is mounted to the first port 20. The first acoustic transducer is mounted to the first port 20 by first threading the wire from the crystal 54 of the first acoustic transducer through a guide 64 and then through washers 66, through a spacer 68 and through a screw top 70. The guide 64, washers 66, spacer 68 and screw top 70, together form a first spring means 56 which creates a bias force against the crystal 54 to press the crystal 54 against the top 60 of the window 40 to better couple the crystal 54 to the window 40 so ultrasonic signals from the crystal 54 effectively pass through the window 40 into the fluid in the pipe 12. The guide 64 which contacts the crystal 54 has bellevue washers 66 placed on it, and then a spacer 68 on top of the washers 66, and then the screw top 70 on top of the spacer 68. This entire structure is then placed together into the first port 20 and the screw top 70 screwed down and tightened to the first port 20 to compress the washers 66 to create the bias force, as the washers 66 attempt to push back to reach their equilibrium position which has been compressed from the screw top 70 being tightened, as shown in FIGS. 7 and 8. In this way, the acoustic transducer is mounted to the housing 14. Wiring from the first transducer 22, second transducer 32 and the temperature sensor 36 is then connected to the transmitter in the junction box 28 by extending along the channel 42 in the housing 14.

The wafer 10 is then placed between two flanges of a pipe 12, and a series of holes 48 in the housing 14 are aligned with the holes 48 of the flanges. Bolts 50 are then inserted through the flanges and series of holes 48 and tightened, as shown in FIG. 14.

Additional ports can be created in the housing 14, if desired. For instance, a pressure transducer can be mounted to the housing 14 in a fifth port. The pressure transducer reaches into the orifice 18 or communicates directly with the orifice 18 without any window 40 or material between it and the orifice 18. The wiring from the pressure transducer runs along the channel 42 to the junction box 28. The acoustic transducers should not be mounted to the top or the bottom of the wafer 10 because of the possibility of air or water or deposits being present in the pipeline. There will result in loss of ultrasonic signal and water results in an erroneous density indication for certain applications. The transducers should be positioned so ultrasonic signals from them do not pass through any air or gas.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An element for placement in a pipe comprising:
    a wafer having an outer surface and an orifice adapted to allow fluid flowing in the pipe to pass through the wafer; and at least a first port extending into the wafer from the outer surface for holding a first acoustic transducer; and
    means for attaching the wafer to the pipe.

2. An element as described in claim 1 wherein the wafer includes at least a second port extending into the wafer from the outer surface for holding a junction box which is in electrical communication with the first transducer.

3. An element as described in claim 2 wherein the wafer includes a third port extending into the wafer from the outer surface for holding a second acoustic transducer which is in electrical communication with the junction box.

4. An element as described in claim 3 wherein the wafer includes a fourth port extending into the wafer from the outer surface for holding a temperature sensor in electrical communication with the junction box.

5. An element as described in claim 4 wherein the first, second, third and fourth ports extend radially inward towards the center of the wafer.

6. An element as described in claim 5 wherein the wafer includes a window disposed between each of the first, third and fourth ports and the orifice.

7. An element as described in claim 6 wherein the wafer has a channel adapted for wires from the first transducer, second transducer and temperature sensor to extend to the junction box.

8. An element as described in claim 7 wherein the first port and the third port are in alignment for ultrasonic signals from the first transistor to communicate with the second transducer after the ultrasonic signals pass through the orifice.

9. An element as described in claim 8 wherein the radius of the orifice is essentially equal to the inside radius of the pipe so there is essentially no disruption of the fluid flowing through the pipe.

10. An element as described in claim 9 including a biasing means for pressing against the first and second acoustic transducer to couple the first and second acoustic transducers to the respective window when the first and second acoustic transducers are attached to the wafer.

11. An element as described in claim 10 wherein the attaching means includes a series of holes dispersed in the wafer and bolts that fit through the holes and are adapted to screw into holes in a flange of the pipe.

12. An element as described in claim 11 wherein the wafer has eyelets and plugs extending into the wafer positioned about the first and third ports to which the eyelets are mounted to the wafer for lifting the wafer.

13. An element as described in claim 12 wherein the first and second acoustic transducers include a crystal disposed in the first and third ports, respectively, when the first and second acoustic transducers are attached to the wafer, and wherein the biasing means includes a first spring means and a second spring means disposed in the first port and the third port, respectively, and adapted to press against the respective crystal to couple the respective crystal against the window of the respective port.

14. An element as described in claim 13 wherein the window has a top and a bottom which are flat and are polished to at least 16 micro inch rms.

15. An element as described in claim 14 wherein each spring means includes a guide which contacts the respective crystal top, a plurality of washers disposed on the guide, a spacer disposed on the washers and a screw top disposed on the spacer and screws to the housing and holds the respective spring means in its respective port.

16. A method for obtaining information about fluid in a pipe comprising the steps of:
    placing a wafer with a flange of a pipe;
    flowing fluid through an orifice of the wafer as the fluid flows through the pipe; and
    transmitting ultrasonic signals from the first acoustic transducer in a first port of the wafer into the fluid in the pipe.

17. A method as described in claim 16 wherein the transmitting step includes the step of transmitting the ultrasonic signals from the first transducer through a window into the fluid in the pipe having a polished surface of at least 16 micro inch rms.

18. A method as described in claim 17 wherein the transmitting step includes the step of maintaining continuously a force against a crystal in the first port of the first acoustic transducer to force the crystal against the window while the crystal produces the ultrasonic signals.

19. A method as described in claim 18 including the step of sending electrical signals between the first transducer and a junction box disposed in a second port of the wafer through wires that extend along a channel in the wafer.

20. A method as described in claim 19 wherein the maintaining step includes the step of screwing a screw top to the first port of the wafer which compresses washers in the first port that in turn press against a guide in the first port that contacts the top of the crystal, with a wire of the crystal extending through the guide, the washers, and the screw top.

21. A method as described in claim 20 including the step of receiving the ultrasonic signals at a second transducer disposed in a second port of the wafer.

22. A method of forming a wafer comprising the steps of:
    drilling a first port radially into a side of a housing to hold a first acoustic transducer;
    drilling an orifice in the center of the housing through which fluid from a pipe can pass; and
    drilling a series of holes axially through the housing about the orifice of the housing.

* * * * *